United States Patent
Sawada

(10) Patent No.: US 8,389,594 B2
(45) Date of Patent: Mar. 5, 2013

(54) SILICONE-MODIFIED ADAMANTANE DERIVATIVE, PHOTO-RADICALLY CURABLE RESIN COMPOSITION, AND METHOD FOR PREPARING PHOTO-RADICALLY CURABLE RESIN COMPOSITION

(75) Inventor: Junichi Sawada, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/284,368

(22) Filed: Oct. 28, 2011

(65) Prior Publication Data
US 2012/0136086 A1 May 31, 2012

(30) Foreign Application Priority Data
Nov. 25, 2010 (JP) .................... 2010-262062

(51) Int. Cl.
*C08F 283/12* (2006.01)
*C08G 77/04* (2006.01)
*C08G 77/38* (2006.01)
*C07F 7/02* (2006.01)

(52) U.S. Cl. .......... 522/99; 522/64; 528/10; 528/25; 556/439

(58) Field of Classification Search ............. 556/439; 522/64, 99; 528/10, 25
See application file for complete search history.

(56) References Cited

U.S. PATENT DOCUMENTS
5,552,506 A 9/1996 Ebbrecht et al.
6,069,186 A 5/2000 Okinoshima et al.

FOREIGN PATENT DOCUMENTS
JP A-11-302348 11/1999
JP B2-3704169 10/2005
JP A-2008-163183 7/2008

*Primary Examiner* — Robert S Loewe
(74) *Attorney, Agent, or Firm* — Oliff & Berridge, PLC

(57) ABSTRACT

There is disclosed a silicone-modified adamantane derivative represented by the following general formula (1),

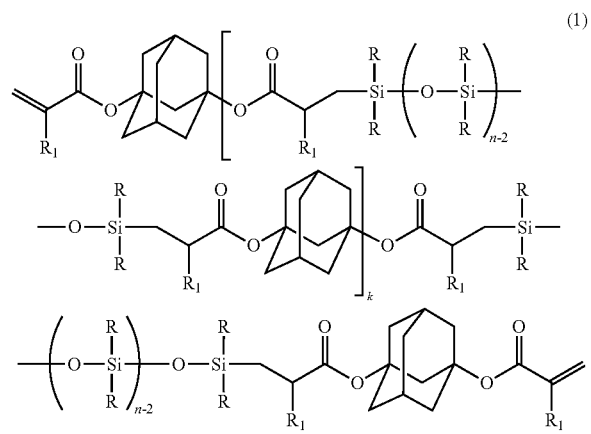

Wherein each $R_1$ independently represents a hydrogen atom or methyl group; each R independently represents a methyl group or phenyl group; n represents an integer from 2 to 1,000; and k represents a number of 0 to 2. There can be a photo-radically curable resin composition by adopting a novel and specific silicone-modified adamantane derivative, which composition is cured by photoirradiation even at a lower intensity of illumination, thereby enabling to obtain a cured product exhibiting not only an excellent moisture resistance but also an excellent adhesiveness to various substrates.

18 Claims, No Drawings

SILICONE-MODIFIED ADAMANTANE DERIVATIVE, PHOTO-RADICALLY CURABLE RESIN COMPOSITION, AND METHOD FOR PREPARING PHOTO-RADICALLY CURABLE RESIN COMPOSITION

BACKGROUND OF THE INVENTION

1. Field of the Invention

The present invention relates to a novel silicone-modified adamantane derivative and a photo-radically curable resin composition useful as a protective coating of various electric and electronic parts, and a method for preparing the photo-radically curable resin composition.

2. Description of the Related Art

As compositions curable by irradiating ultraviolet rays or the like thereto, there have been already known: a composition containing an acrylic(methacrylic)-modified silicone resin (Japanese Patent Laid-Open (kokai) No. 2008-163183); a composition containing an organopolysiloxane having an acrylic group or methacrylic group at each end of a molecule chain, and a photopolymerization initiator (Japanese Patent Laid-Open (kokai) No. H11-302348); and the like.

However, these compositions have been low in adhesiveness to a substrate, and failed to possess a sufficient moisture resistance, so that the compositions have been insufficient for usage as a protective coating of a liquid crystal electrode, organic EL electrode, and plasma display electrode, which are susceptible to ultraviolet rays or the like.

Therefore, such a material has been demanded, which is excellent in adhesiveness to a substrate, and possesses a sufficient moisture resistance, and is thus useful as a protective coating of various electric and electronic parts (particularly, liquid crystal electrode, organic EL electrode, plasma display electrode, and the like).

SUMMARY OF THE INVENTION

The present invention has been carried out in view of the above circumstances, and it is therefore an object of the present invention to provide a photo-radically curable resin composition by adopting a novel and specific silicone-modified adamantane derivative, which composition is cured by photoirradiation even at a lower intensity of illumination, thereby enabling to obtain a cured product exhibiting not only an excellent moisture resistance but also an excellent adhesiveness to various substrates.

To achieve the above object, the present invention provides a silicone-modified adamantane derivative represented by the following general formula (1),

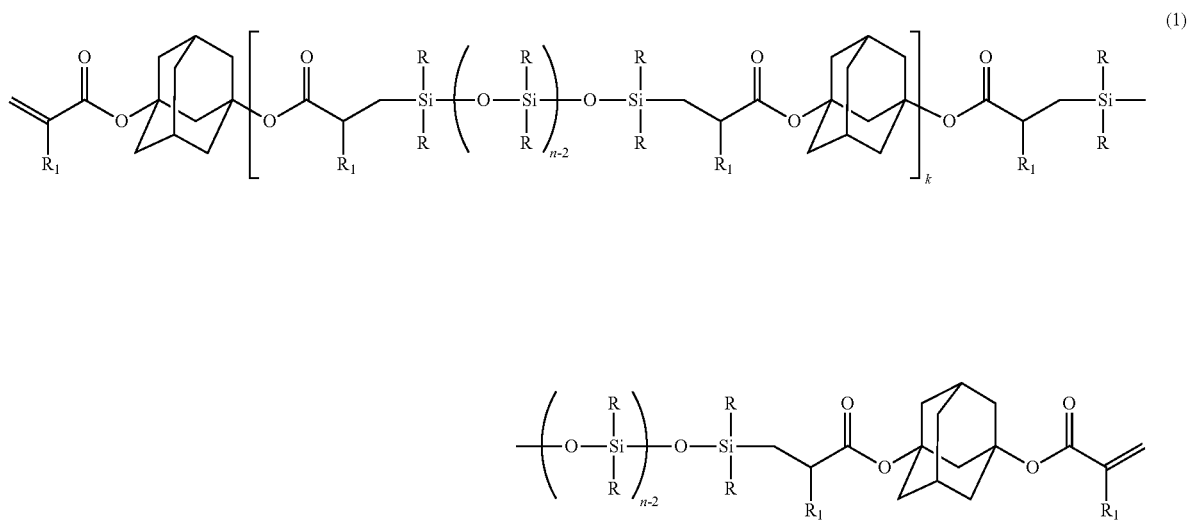

wherein each $R_1$ independently represents a hydrogen atom or methyl group;

each R independently represents a methyl group or phenyl group;

n represents an integer from 2 to 1,000; and k represents a number of 0 to 2.

Such a silicone-modified adamantane derivative is a photo-radically polymerizable compound, which contains an acryl group and/or methacryl group and which is thus highly sensitive to a light source such as ultraviolet rays or the like, so that the silicone-modified adamantane derivative is capable of being excellently cured (radically polymerized) by ultraviolet irradiation even at a lower intensity of illumination.

In this case, it is preferable that the silicone-modified adamantane derivative is represented by the following general formula (2),

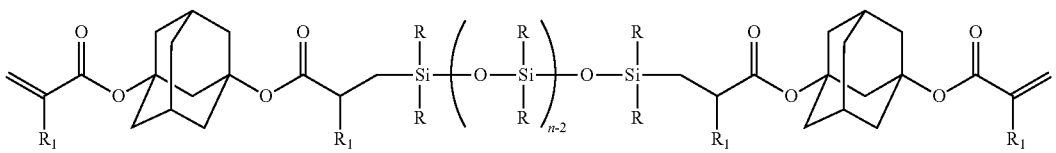

wherein n, R, and $R_1$ represent the same meaning as before.

The silicone-modified adamantane derivative represented by the general formula (2) can be synthesized inexpensively and readily, and is thus preferable.

Further, the present invention provides a photo-radically curable resin composition containing the following components (A), (B), and (C):

(A) a silicone-modified adamantane derivative represented by the following general formula (1):

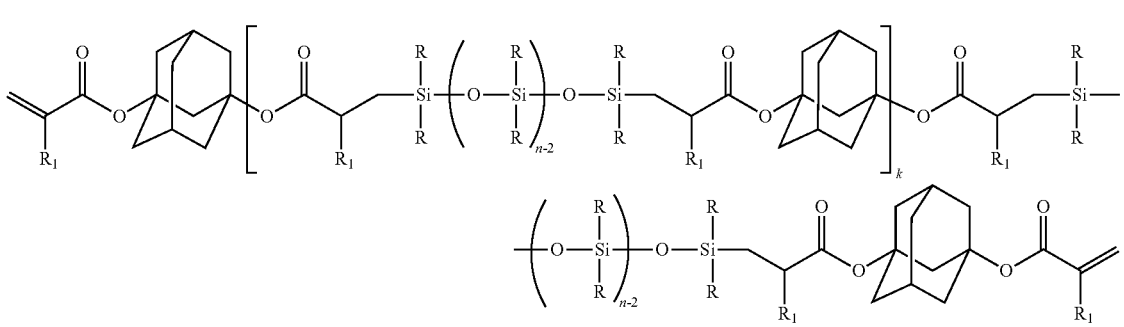

wherein each $R_1$ independently represents a hydrogen atom or methyl group;

each R independently represents a methyl group or phenyl group;

n represents an integer from 2 to 1,000; and k represents a number of 0 to 2;

(B) a photo-radical initiator; and (C) a radical chain transfer agent,

Such a photo-radically curable resin composition is readily cured at a lower intensity of illumination, and is capable of obtaining a cured product having not only an excellent moisture resistance but also an excellent adhesiveness to various substrates, so that the photo-radically curable resin composition is particularly useful as a protective coating of a liquid crystal electrode, organic EL electrode, and plasma display electrode, which are susceptible to ultraviolet rays or the like.

In this case, it is preferable that the silicone-modified adamantane derivative (A) is a silicone-modified adamantane derivative represented by the following general formula (2), sition containing the silicone-modified adamantane derivative represented by the general formula (2) is economically advantageous.

In this case, it is preferable that the photo-radical initiator (B) is one kind or two or more kinds of compounds selected from:

(B1) a ketone compound;

(B2) an acyl phosphine compound; and (B3) a thioxanthone compound.

Although it is possible to use, as the photo-radical initiator (B), any compound configured to generate a polymerization active species by photoirradiation such as irradiation of ultraviolet rays or the like, it is possible to adopt one kind or two or more kinds of compounds selected from the ketone compound (B1), acyl phosphine compound (B2), and thioxanthone compound (B3).

Further, in this case, it is preferable that the photo-radically curable resin composition contains:

the component (A) in an amount of 30 to 99 mass %;

the component (B) in an amount of 0.05 to 15 mass %; and the component (C) in an amount of 0.01 to 10 mass %.

The photo-radically curable resin composition containing the components in the above amounts, respectively, is made to be highly sensitive to a light source such as ultraviolet rays or the like, thereby achieving an increased curing rate.

In turn, the present invention provides a method for preparing the photo-radically curable resin composition, comprising the step of:

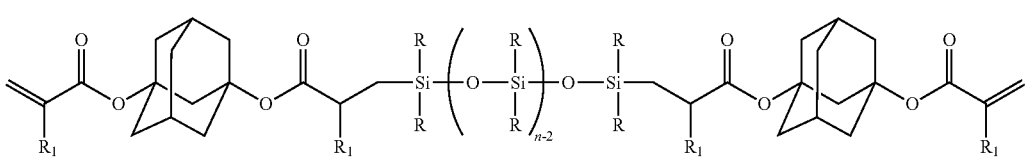

wherein n, R, and $R_1$ represent the same meaning as before.

The silicone-modified adamantane derivative represented by the general formula (2) can be synthesized inexpensively and readily, so that the photo-radically curable resin compomixing a mixture obtained by homogeneously mixing the photo-radical initiator (B) and the radical chain transfer agent (C), with the silicone-modified adamantane derivative (A).

Mixing the photo-radical initiator (B) with the radical chain transfer agent (C) and homogenizing them, provides a stable mixture which is free from deposition of the photo-radical initiator and the radical chain transfer agent even at a room temperature, thereby enabling to conduct the mixing of the mixture with the silicone-modified adamantane derivative (A) at the room temperature. Further, it is possible to suppress recrystallization of the photo-radical initiator and radical chain transfer agent in the photo-radically curable resin composition.

Since the photo-radically curable resin composition containing the silicone-modified adamantane derivative of the present invention is readily cured at a lower intensity of illumination, and is capable of providing a cured product having not only an excellent moisture resistance but also an excellent adhesiveness to various substrates, so that the photo-radically curable resin composition is particularly useful as a protective coating of a liquid crystal electrode, organic EL electrode, and plasma display electrode, which are susceptible to ultraviolet rays or the like.

DETAILED DESCRIPTION OF THE PREFERRED EMBODIMENTS

The present invention will be explained in more detail hereinafter.

The present inventor has earnestly conducted investigation so as to achieve the above object, and has resultingly found out that the silicone-modified adamantane derivative represented by the following general formula (1), as a novel photo-radically polymerizable compound containing an acryl group and/or methacryl group, exhibits a high sensitivity to a light source such as ultraviolet rays and the like,

[Photo-Radically Curable Resin Composition]

The photo-radically curable resin composition of the present invention contains at least the following components (A), (B), and (C).

(A) Silicone-Modified Adamantane Derivative:

The silicone-modified adamantane derivative of the present invention is a photo-radically polymerizable compound containing an acryl group and/or methacryl group and thus exhibits a higher sensitivity to a light source such as ultraviolet rays and the like, so that the silicone-modified adamantane derivative is capable of being cured by ultraviolet irradiation even at a lower intensity of illumination. This silicone-modified adamantane derivative contains a silicone chain comprising repeating units of siloxane represented by $R_2SiO$, and the number of silicon atoms of the silicone chain (i.e., the polymerization degree "n") is 2 to 1,000. "n" is preferably 2 to 100, and more preferably 2 to 20.

The silicone-modified adamantane derivative of the present invention is obtainable by hydrosilylating a di(meth)acryl adamantane derivative represented by the following general formula (3) and a linear organohydrogen polysiloxane represented by the following general formula (4) in the presence of a rhodium catalyst, based on the method disclosed in Japanese Patent No. 3704169. The di(meth)acryl adamantane derivative represented by the following general formula (3) is a compound, which is obtained by modifying adamantane with a (meth)acrylic acid ester residue,

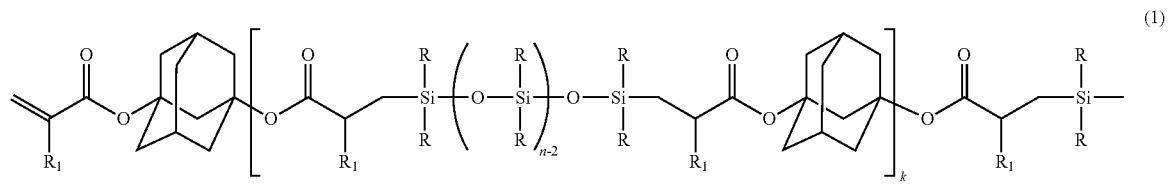

(1)

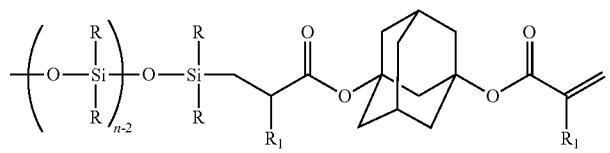

wherein
each $R_1$ independently represents a hydrogen atom or methyl group;
each R independently represents a methyl group or phenyl group;
n represents an integer from 2 to 1,000; and
k represents a number of 0 to 2.

The present inventor has further found out that the photo-radically curable resin composition containing such a silicone-modified adamantane derivative is capable of providing a cured product simultaneously exhibiting an excellent moisture resistance and an excellent adhesiveness even under a condition of a lower intensity of illumination, thereby narrowly carried out the present invention.

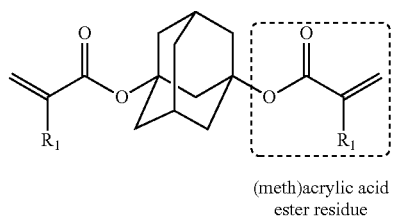

(3)

(meth)acrylic acid ester residue wherein each $R_1$ represents a hydrogen atom or methyl group.

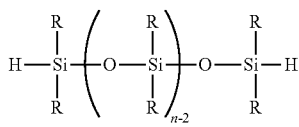

(4)

wherein n represents an integer of 2 to 1,000, preferably 2 to 100, more preferably 2 to 20, and each R independently represents a methyl group or phenyl group.

For example, organohydrogen polysiloxane represented by the formula (4) is dropped with stirring, into a mixture, being heated at 60° C. to 130° C., preferably at 80° C. to 110° C. with stirring, of: the di(meth)acryl adamantane derivative represented by the formula (3); a rhodium catalyst in such an amount that the rhodium equivalent is made to be 5 to 200 ppm based on the total mass of the di(meth)acryl adamantane derivative and the organohydrogen polysiloxane; BHT (dibutylhydroxytoluene), as an antioxidant, in an amount of 200 to 5,000 ppm relative to the di(meth)acryl adamantane derivative; and tri(meth)acryl isocyanurate, and toluene in the same amount as it, as a cooperative solvent; in such an amount of the organohydrogen polysiloxane that di(meth)acryl adamantane derivative: organohydrogen polysiloxane=1:0.25 to 1:1 (molar ratio), preferably 1:0.5 to 1:0.7 (molar ratio). Thereafter, the resultant mixture is stirred for 3 to 5 hours at the above-mentioned temperature, followed by removal of the toluene by stripping under reduced pressure, thereby allowing to obtain the intended silicone-modified adamantane derivative.

Examples of the rhodium catalyst to be used for hydrosilylation exemplarily include RhCl(Ph$_3$P)$_3$, RhCl$_3$.3H$_2$O, [RhClEt$_2$]$_2$, [RhCl(cod)]$_2$, and the like (where Ph is a phenyl group, Et is an ethyl group, and cod is cyclooctadiene).

The above described method allows to obtain the silicone-modified adamantane derivative represented by the following general formula (1),

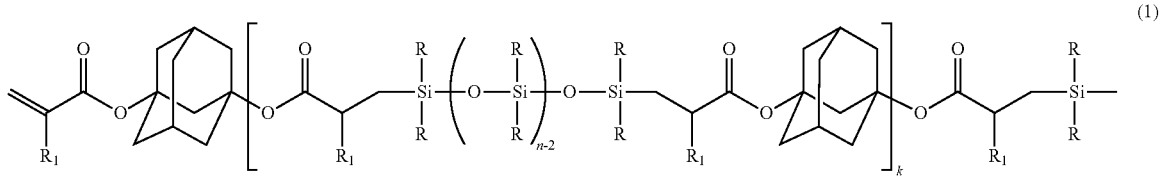

(1)

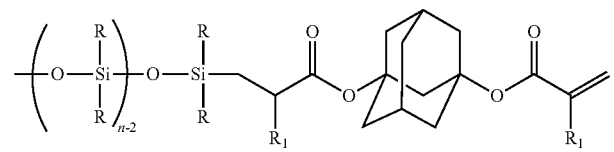

wherein
k represents a number of 0 to 2; and n, R, and R$_1$ represent the same meaning as before.

Particularly, the silicone-modified adamantane derivative represented by the following general formula (2) is preferable, by virtue of facilitated synthesis thereof,

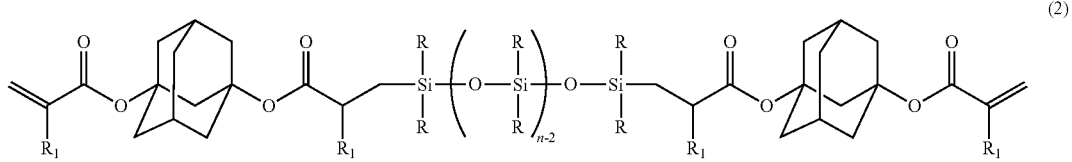

(2)

wherein n, R, and $R_1$ represent the same meaning as before.

The component (A) is to be preferably blended in an amount of 30 to 99 mass %, preferably 70 to 98 mass %, in the photo-radically curable resin composition. By blending it in such a ratio, the photo-radically curable resin composition of the present invention is made to be more sensitive to a light source such as ultraviolet rays or the like, thereby enhancing its curing rate. It is noted that, although the di(meth)acryl adamantane derivative is occasionally left unreacted in the above reaction, or the (meth)acryl group in the side-chain of the compound represented by the formula (1) is occasionally reacted with the organohydrogen polysiloxane to produce a compound, such a residue or compound may be contained, without removal, in the photo-radically curable resin composition.

(B) Photo-Radical Initiator:

Although any compound is usable as the photo-radical initiator insofar as the compound generates a polymerization active species by photoirradiation such as irradiation of ultraviolet rays or the like, it is specifically possible to use one kind or two or more kinds of compounds selected from the ketone compound (B1), the acyl phosphine compound (B2), and the thioxanthone compound (B3).

Usable as the ketone compound (B1) without limitation are those which can each be used as a photo-radical initiator, and examples thereof specifically include: α-hydroxycyclohexylphenylketone; 2-hydroxy-2-methyl-1-phenylpropanone; 2-hydroxy-2-methyl-1-(4-isopropylphenyl)propanone; 2-hydroxy-2-methyl-1-(4-dodecylphenyl)propanone; and 2-hydroxy-2-methyl-1-[(2-hydroxyethoxy)phenyl]propanone; benzophenone; 2-methylbenzophenone; 3-methylbenzophenone; 4-methylbenzophenone; 4-methoxybenzophenone; 2-chlorobenzophenone; 4-chlorobenzophenone; 4-bromobenzophenone; 2-carboxybenzophenone; 2-ethoxycarbonylbenzophenone; benzophenone tetracarboxylate or its tetramethyl ester; 4,4'-bis(dialkylamino)benzophenones (4,4'-bis(dimethylamino)benzophenone, 4,4'-bis(dicyclohexylamino)benzophenone, 4,4'-bis(diethylamino)benzophenone, and 4,4'-bis(dihydroxyethylamino)benzophenone, for example); 4-methoxy-4'-dimethylaminobenzophenone; 4,4'-dimethoxybenzophenone; 4-dimethylaminobenzophenone; 4-dimethylaminoacetophenone; benzyl; anthraquinone; 2-t-butylanthraquinone; 2-methylanthraquinone; phenanthraquinone; fluorenone; 2-benzyl-dimethylamino-1-(4-morpholinophenyl)-1-butanone; 2-methyl-1-[4-(methylthio)phenyl]-2-morpholino-1-propanone; 2-hydroxy-2-methyl-[4-(1-methylvinyl)phenyl]propanol oligomer; benzoin; benzoin ethers (benzoin methyl ether, benzoin ethyl ether, benzoin propyl ether, benzoin isopropyl ether, benzoin phenyl ether, benzyldimethylketal, for example); acridone; chloro acridone; N-methyl acridone; N-butyl acridone; and N-butyl-chloro acridone.

Usable as the acyl phosphine compound (B2) without limitation are those which can each be used as a photo-radical initiator, and examples thereof specifically include: 2,4,6-trimethylbenzoyl-diphenylphosphineoxide; 2,6-dimethoxybenzoyl-diphenylphosphineoxide; 2,6-dichlorobenzoyl-diphenylphosphineoxide; 2,4,6-trimethylbenzoyl-methoxyphenylphosphineoxide; 2,4,6-trimethylbenzoyl-ethoxyphenylphosphineoxide; 2,3,5,6-tetramethylbenzoyl-diphenylphosphineoxide; and benzoyl-di-(2,6-dimethylphenyl)phosphonate. Examples of bisacylphosphineoxides include: bis-(2,6-dichlorobenzoyl) phenylphosphineoxide; bis-(2,6-dichlorobenzoyl)-2,5-dimethylphenylphosphineoxide; bis-(2,6-dichlorobenzoyl)-4-propylphenylphosphineoxide; bis-(2,6-dichlorobenzoyl)-1-naphthylphosphineoxide; bis-(2,6-dimethoxybenzoyl) phenylphosphineoxide; bis-(2,6-dimethoxybenzoyl)-2,4,4-trimethylpentylphosphineoxide; bis-(2,6-dimethoxybenzoyl)-2,5-dimethylphenylphosphineoxide; bis-(2,4,6-trimethylbenzoyl)phenylphosphineoxide; and (2,5,6-trimethylbenzoyl)-2,4,4-trimethylpentylphosphineoxide.

Usable as the thioxanthone compound (B3) without limitation are those, which can each be used as a photo-radical initiator, and examples thereof specifically include: 2-isopropylthioxanthone, 4-isopropylthioxanthone, 2,4-diethylthioxanthone, 2,4-dichlorothioxanthone, and 1-chloro-4-propoxythioxanthone.

The photopolymerization initiators (B1) to (B3) may each be used solely, or may be used combinedly in two or more kinds. They are to be preferably blended in such an amount that the total mass of the component (B) (total mass of (B1) to (B3)) is made to be 0.05 to 15 mass %, preferably 0.5 to 6 mass %, in the photo-radically curable resin composition.

(C) Radical Chain Transfer Agent:

The radical chain transfer agent is used to reactivate those polymerization active species trapped by an inactive radical scavenger such as oxygen. Any compound may be used without particularly limited insofar having such a function, and examples of the radical chain transfer agent exemplarily include: N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, 4-N,N-dimethylaminobenzoic acid ethyl ester, 4-N,N-dimethylaminobenzoic acid methyl ester, N,N-dimethylaminobenzoic acid n-butoxyethyl ester, 4-N,N-dimethylaminobenzoic 2-(methacryloyloxy)ethyl ester, 4-N,N-dimethylaminobenzophenone, [4-(methylphenylthio)phenyl]phenylmethanone, trimethylamine, triethylamine, N-methyldiethanolamine, N-ethyldiethanolamine, N-n-butyldiethanolamine, N-lauryldiethanolamine, triethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, and the like. Particularly preferable examples of the chain transfer agent include 2-ethylhexyl-4-dimethyl aminobenzoate, [4-(methylphenylthio) phenyl]phenylmethanone, and the like. These radical chain transfer agents may each be used solely, or may be used combinedly in two or more kinds.

The radical chain transfer agent (C) is to be preferably blended in the photo-radically curable resin composition, in an amount of 0.01 to 10 mass %, preferably 0.4 to 5 mass %.

It is noted that the above noted components (A), (B), and (C) as those to be used in the photo-radically curable resin composition of the present invention, may each include a single compound or multiple kinds of compounds.

Other Components:

To further improve the adhesiveness of the cured product obtained from the photo-radically curable resin composition of the present invention, it is possible to further add an adhesive aid into the photo-radically curable resin composition. Examples thereof specifically include: those compounds each having a cyanoacrylate structure like an alkyl ester of cyanoacrylic acid, such as methylcyanoacrylate, ethylcyanoacrylate, propylcyanoacrylate, and butylcyanoacrylate; alkoxysilanes each containing an epoxy functional group, as represented by β-glycidoxyethyl-trimethoxysilane, α-glycidoxypropyl-trimethoxysilane, β-glycidoxypropyl-trimethoxysilane, γ-glycidoxypropyl-trimethoxysilane, α-glycidoxybutyl-trimethoxysilane, β-glycidoxybutyl-trimethoxysilane, γ-glycidoxybutyl-trimethoxysilane, δ-glycidoxybutyl-trimethoxysilane, (3,4-epoxycyclohexyl)methyl-trimethoxysilane, β-(3,4-epoxycyclohexyl)ethyl-trimethoxysilane, γ-(3,4-epoxycyclohexyl)propyl-trimethoxysilane, δ-(3,4-epoxycyclohexyl)butyl-trimethoxysilane; and silane coupling agents, which are partial hydrolytic condensates of them, respectively. The adhesive aid may include one having a structure of multiple kinds of above described structures which are combined with one another by chemical bonds. The adhesive aid is to be blended in the photo-radically curable resin composition, preferably in a blending amount of 0.1 to 10 mass %, preferably 0.5 to 5 mass %.

Further, it is possible to blend a solvent into the photo-radically curable resin composition of the present invention, as required. Preferable solvents are nonpolar hydrocarbon-based solvents each having 5 to 15 carbon atoms, such as n-pentane, n-hexane, n-heptane, isooctane, cyclopentane, cyclohexane, and the like. It is also possible to adopt a hetero-containing solvent (i.e., a solvent containing a heteroatom other than carbon and hydrogen), and usable examples thereof include: ether-based solvents and ester-based solvents, such as diethyl ether, tetrahydrofuran, 1,4-dioxane, acetone, ethyl acetate, butyl acetate; and silane-based solvents and siloxane-based solvents such as hexamethyldisilane, and hexamethyldisiloxane, respectively. Further, it is possible to adopt a fluorine-containing solvent, such as fluoroalkane, fluoroalkyl ether, and the like. It is preferable to add the solvent into the photo-radically curable resin composition, in an amount of 0.1 to 60 mass %, preferably 30 to 50 mass %, because the solubility of the photo-radical initiator therein is improved then.

[Method for Preparing Photo-Radically Curable Resin Composition]

The photo-radically curable resin composition can be produced by mixing: a mixture obtained by previously mixing the photo-radical initiator (B) and the radical chain transfer agent (C) with each other at a high temperature of 50 to 150° C., preferably 100 to 150° C., to heat, dissolve, and homogenize them; with the silicone-modified adamantane derivative (A); at 5° C. to 45° C., preferably at 10° C. to 40° C. Previously mixing the photo-radical initiator (B) with the radical chain transfer agent (C) and homogenizing them, provides a stable mixture which is free from deposition of the photo-radical initiator and the radical chain transfer agent even at a room temperature, thereby enabling to conduct the mixing of the mixture with the silicone-modified adamantane derivative (A) at the room temperature. Further, by production according to the above method, it is possible to suppress recrystallization of the photo-radical initiator and radical chain transfer agent in the photo-radically curable resin composition.

The photo-radically curable resin composition obtained in this way contains the silicone-modified adamantane derivative (A), so that this composition is readily cured by photoirradiation thereto even for a short time, and the resultingly cured product possesses not only an excellent moisture resistance but also an excellent adhesiveness to various substrates. Thus, the composition is useful not only as a protective coating of a liquid crystal electrode, organic EL electrode, and plasma display electrode, which are susceptible to ultraviolet rays or the like, but also as a protective coating of various electric and electronic parts.

EXAMPLES

Although the present invention will be described hereinafter in more detail based on Examples and Comparative Examples, the present invention is not limited to these Examples. Further, the term "part(s)" in the following description means a mass part(s), $M^H$ means an $R_2HSiO_{1/2}$ unit, and D means an $R_2SiO$ unit.

Example 1

Preparation of Silicone-Modified Adamantane Derivative

Charged into a separable flask provided with a stirrer, a titration funnel, a thermometer, and a refluxing cooler, were: 552.28 g of diacryl adamantane; 0.23 g of chlorotris(triphenylphosphine)rhodium (I) [RhCl((Ph$_3$P)$_3$] (rhodium equivalent: 20 ppm, based on a total mass of polydimethylsiloxane and diacryl adamantane); 1.10 g of BHT (2,000 ppm relative to diacryl adamantane); and 552.28 g of toluene; followed by stirring, and heating to 80° C. Dropped with stirring into the flask was 726 g of polydimethylsiloxane represented by $M^H_2D_8$ (diacryl adamantane: polydimethylsiloxane=2:1 (molar ratio)), at a dropping rate of 10 g/min or less. After termination of dropping, stirring was conducted at 80° C. for 3 hours, followed by removal of the toluene by stripping under reduced pressure, thereby obtaining 1,214 g of a liquid product (inclusion of unreacted diacryl adamantane of less than 10% was confirmed by GPC).

As a result of measurements by $^1$H-NMR and GPC, the obtained product was confirmed to be silicone-modified adamantane represented by the following formula (5). It is noted that $^1$H-NMR was conducted by using the following apparatus:

$^1$H-NMR: AVANCE III 400 Type (manufactured by Bruker BioSpin K.K.)

GPC: SC-8020 (manufactured by TOSOH CORPORATION)

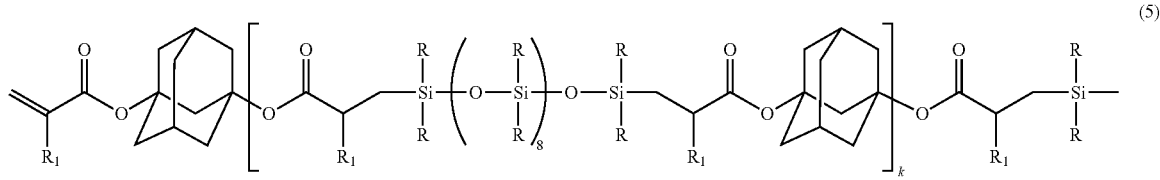

(5)

($k \approx 1$, $R=CH_3$, and $R_1=H$)

Example 2

Preparation of Photo-Radically Curable Resin Composition

Mutually mixed were: 2 parts of 2-methyl-1-[4-(methylthio)phenyl]-2-morpholino-1-propanone (produced by Ciba Speciality Chemicals Inc., product name: IRGACURE 907) as the photo-radical initiator (B); and 0.5 part of [4-(methylphenylthio)phenyl]phenylmethanone (produced by Nippon Kayaku Co., Ltd., product name: KAYACURE EMS), as the radical chain transfer agent (C); followed by heating and dissolving, at 100° C. for 10 minutes. The resultant liquid was cooled down to a room temperature, and was added into 100 parts of the silicone-modified adamantane represented by the above formula (5), to obtain a photo-radically curable resin composition by a stirring and defoaming operation.

Example 3

Prepared was silicone-modified adamantane in the same manner as Example 1, except that polydimethylsiloxane represented by $M^H{}_2D_3$ was adopted instead of the polydimethylsiloxane represented by $M^H{}_2D_8$ in Example 1. As a result of measurements by $^1$H-NMR and GPC, the obtained product was confirmed to be silicone-modified adamantane represented by the following formula (6) (inclusion of unreacted diacryl adamantane of less than 10% was confirmed by GPC). This compound was used to prepare a photo-radically curable resin composition, similarly to Example 2:

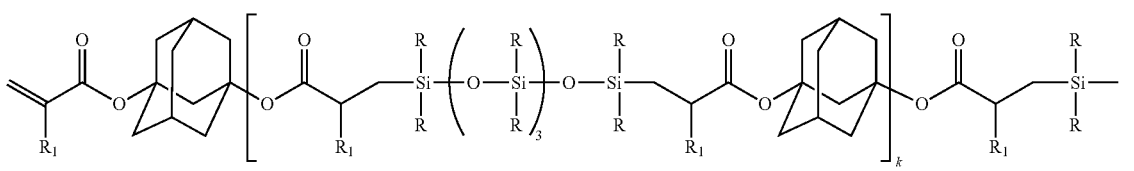

(6)

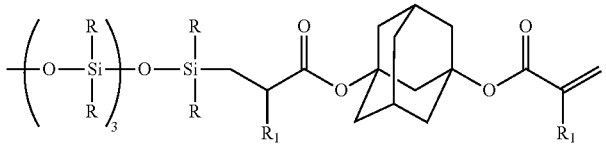

($k \approx 1.5$, $R=CH_3$, and $R_1=H$)

Example 4

Prepared was silicone-modified adamantane in the same manner as Example 1, except that polydimethylsiloxane represented by $M^H{}_2D_{18}$ was adopted instead of the polydimethylsiloxane represented by $M^H{}_2D_8$ in Example 1. As a result of measurements by $^1$H-NMR and GPC, the obtained product was confirmed to be silicone-modified adamantane represented by the following formula (7) (inclusion of unreacted diacryl adamantane of less than 10% was confirmed by GPC). This compound was used to prepare a photo-radically curable resin composition, similarly to Example 2:

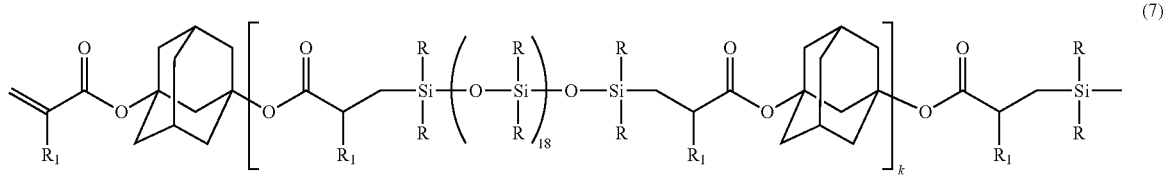

(7)

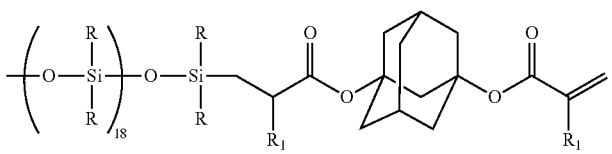

(k≈1, R=CH₃, and R₁=H)

Comparative Example 1

Prepared was a photo-radically curable resin composition similarly to Example 2, except that acrylic-modified silicone represented by the following formula (8) as disclosed in Japanese Patent Laid-Open (kokai) No. 2008-163183 was used instead of 100 parts of the silicone-modified adamantane represented by the formula (5),

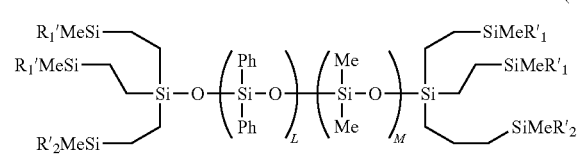

(8)

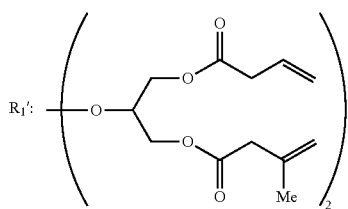

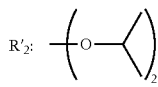

L:M = 3:1 wherein Me represents a methyl group, Ph represents a phenyl group, L=integer of 700 to 850, and M=integer of 150 to 350.

The resin compositions were each poured into a mold having a depth of 1 mm, a width of 120 mm, and a length of 170 mm, and subjected to irradiation of ultraviolet rays (energy amount: 200 mJ) for 2 seconds by a conveyor device having two mercury and metal halide lamps (intensity of illumination: 40 W/cm²), thereby obtaining cured products, respectively.

[Evaluation of Hardness]

The obtained cured products were each subjected to measurement of its hardness by a spring type A style tester, in conformity to JIS K 6301.

[Evaluation of Water Vapor Permeability]

The obtained cured products were each subjected to measurement of its water vapor permeability, in conformity to JIS Z 0208.

[Evaluation of Adhesiveness to Glass]

Formed on a slide glass of 25 mm width and 75 mm length, was a groove of 0.2 mm depth and 2 mm width by means of masking tapes, and each resin composition was poured into the groove by a syringe, followed by placement of a glass chip of 2 mm×2 mm thereon and by irradiation of ultraviolet rays (energy amount: 200 mJ) thereto for 2 seconds by a conveyor device having two mercury and metal halide lamps (intensity of illumination: 40 W/cm²), thereby obtaining a cured product. The obtained cured products were each tested for its adhesiveness to glass, in a manner to split the adhered piece at a rate of 0.2 mm/sec by adopting a universal bond tester (DAGE SERIES 4000), thereby measuring an adhesivity of each cured product. Obtained results are listed in Table 1.

TABLE 1

| | Hardness (Type A) | Water Vapor Permeability (g/mm² · 24 h) | Adhesivity to glass (kg/cm²) |
|---|---|---|---|
| Example 2 | 90 | 8 | 115 |
| Example 3 | 88 | 11 | 122 |
| Example 4 | 85 | 10 | 123 |
| Comparative Example 1 | 79 | 81 | 18 |

As apparent from the results of Table 1, it was confirmed that the photo-radically curable resin composition of the present invention is not only sufficiently cured at a lower intensity of illumination, but also configured to exhibit an excellent curability under a curing condition adopting ultraviolet rays or the like, in a manner to possess a lower water vapor permeability (excellent moisture resistance) and an excellent adhesiveness to a substrate (glass). Contrary, the photo-radically curable resin composition of Comparative Example 1, which adopted the acrylic-modified silicone disclosed in Japanese Patent Laid-Open (kokai) No. 2008-163183, was resultingly insufficient in hardness, moisture resistance, and adhesiveness.

It is noted that the present invention is not limited to the above embodiments. The embodiments are illustrative, and whatever have substantially the same configuration as the technical concept recited in the claims of the present application and exhibit the same functions and effects, are embraced within the technical scope of the present invention.

What is claimed is:

1. A silicone-modified adamantane derivative represented by the following general formula (1),

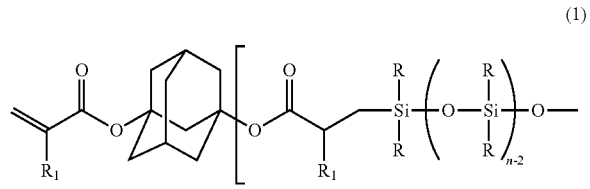

(1)

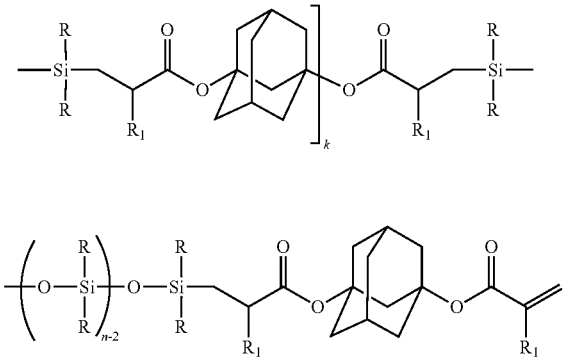

-continued wherein each $R_1$ independently represents a hydrogen atom or methyl group;

each R independently represents a methyl group or phenyl group;

n represents an integer from 2 to 1,000; and k represents a number of 0 to 2.

2. The silicone-modified adamantane derivative according to claim 1, wherein the silicone-modified adamantane derivative is represented by the following general formula (2),

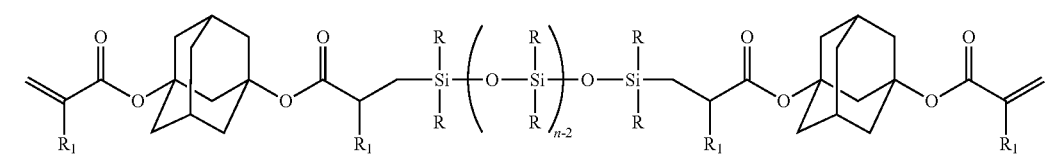

(2)

wherein n, R, and $R_1$ represent the same meaning as before.

3. A photo-radically curable resin composition containing the following components (A), (B), and (C):

(A) a silicone-modified adamantane derivative represented by the following general formula (1),

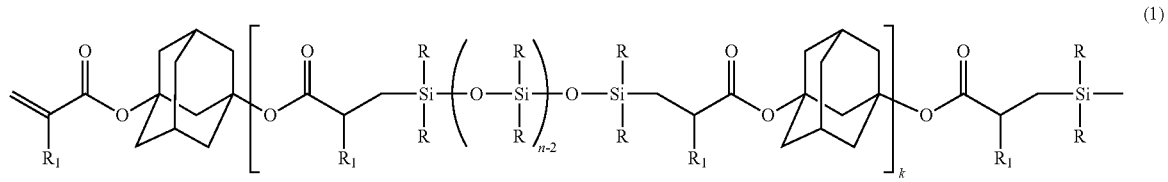

(1)

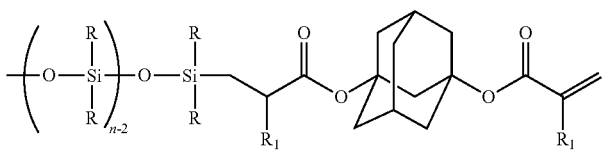

wherein
each $R_1$ independently represents a hydrogen atom or methyl group;
each R independently represents a methyl group or phenyl group;
n represents an integer from 2 to 1,000; and
k represents a number of 0 to 2,
(B) a photo-radical initiator; and
(C) a radical chain transfer agent.

4. The photo-radically curable resin composition according to claim 3, wherein the silicone-modified adamantane derivative (A) is a silicone-modified adamantane derivative represented by the following general formula (2),

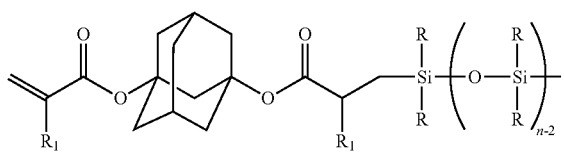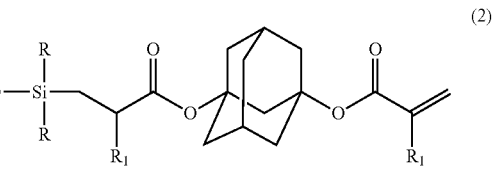

(2)

wherein n, R, and $R_1$ represent the same meaning as before.

5. The photo-radically curable resin composition according to claim 4, wherein the photo-radical initiator (B) is one kind or two or more kinds of compounds selected from:
(B1) a ketone compound;
(B2) an acyl phosphine compound; and
(B3) a thioxanthone compound.

6. The photo-radically curable resin composition according to claim 5, wherein the photo-radically curable resin composition contains:
the component (A) in an amount of 30 to 99 mass %;
the component (B) in an amount of 0.05 to 15 mass %; and
the component (C) in an amount of 0.01 to 10 mass %.

7. A method for preparing the photo-radically curable resin composition according to claim 6, comprising the step of:
mixing a mixture obtained by homogeneously mixing the photo-radical initiator (B) and the radical chain transfer agent (C), with the silicone-modified adamantane derivative (A).

8. A method for preparing the photo-radically curable resin composition according to claim 5, comprising the step of:
mixing a mixture obtained by homogeneously mixing the photo-radical initiator (B) and the radical chain transfer agent (C), with the silicone-modified adamantane derivative (A).

9. The photo-radically curable resin composition according to claim 4, wherein the photo-radically curable resin composition contains:
the component (A) in an amount of 30 to 99 mass %;
the component (B) in an amount of 0.05 to 15 mass %; and
the component (C) in an amount of 0.01 to 10 mass %.

10. A method for preparing the photo-radically curable resin composition according to claim 9, comprising the step of:
mixing a mixture obtained by homogeneously mixing the photo-radical initiator (B) and the radical chain transfer agent (C), with the silicone-modified adamantane derivative (A).

11. A method for preparing the photo-radically curable resin composition according to claim 4, comprising the step of:
mixing a mixture obtained by homogeneously mixing the photo-radical initiator (B) and the radical chain transfer agent (C), with the silicone-modified adamantane derivative (A).

12. The photo-radically curable resin composition according to claim 3, wherein the photo-radical initiator (B) is one kind or two or more kinds of compounds selected from:
(B1) a ketone compound;
(B2) an acyl phosphine compound; and
(B3) a thioxanthone compound.

13. The photo-radically curable resin composition according to claim 12, wherein the photo-radically curable resin composition contains:
the component (A) in an amount of 30 to 99 mass %;
the component (B) in an amount of 0.05 to 15 mass %; and
the component (C) in an amount of 0.01 to 10 mass %.

14. A method for preparing the photo-radically curable resin composition according to claim 13, comprising the step of:
mixing a mixture obtained by homogeneously mixing the photo-radical initiator (B) and the radical chain transfer agent (C), with the silicone-modified adamantane derivative (A).

15. A method for preparing the photo-radically curable resin composition according to claim 12, comprising the step of:
mixing a mixture obtained by homogeneously mixing the photo-radical initiator (B) and the radical chain transfer agent (C), with the silicone-modified adamantane derivative (A).

16. The photo-radically curable resin composition according to claim 3, wherein the photo-radically curable resin composition contains:
the component (A) in an amount of 30 to 99 mass %;
the component (B) in an amount of 0.05 to 15 mass %; and
the component (C) in an amount of 0.01 to 10 mass %.

17. A method for preparing the photo-radically curable resin composition according to claim 16, comprising the step of:
mixing a mixture obtained by homogeneously mixing the photo-radical initiator (B) and the radical chain transfer agent (C), with the silicone-modified adamantane derivative (A).

18. A method for preparing the photo-radically curable resin composition according to claim 3, comprising the step of:
mixing a mixture obtained by homogeneously mixing the photo-radical initiator (B) and the radical chain transfer agent (C), with the silicone-modified adamantane derivative (A).

* * * * *